United States Patent [19]

Seneker et al.

[11] Patent Number: 5,175,350
[45] Date of Patent: Dec. 29, 1992

[54] MELT CRYSTALLIZATION PROCESS FOR PREPARING HIGH TRANS, TRANS-ISOMER CONTAINING 4,4'-DIISOCYANATO DICYCLOHEXYLMETHANE

[75] Inventors: Stephen D. Seneker, Paden City; Kenneth L. Dunlap, New Martinsville, both of W. Va.; Michael K. Lowery, Pittsburgh, Pa.; Terry A. Potter, New Martinsville, W. Va.

[73] Assignee: Miles Inc., Pittsburgh, Pa.

[21] Appl. No.: 836,639

[22] Filed: Feb. 14, 1992

Related U.S. Application Data

[63] Continuation of Ser. No. 654,862, Feb. 13, 1991, abandoned, which is a continuation-in-part of Ser. No. 513,698, Apr. 24, 1990, abandoned.

[51] Int. Cl.$^5$ .......................................... C07C 263/20
[52] U.S. Cl. ................................. 560/352; 521/163; 560/330
[58] Field of Search ................................. 560/352, 330

[56] References Cited

U.S. PATENT DOCUMENTS

| | | | |
|---|---|---|---|
| 2,494,563 | 1/1950 | Kirk, Jr. et al. | 564/462 |
| 2,606,925 | 8/1952 | Whitman et al. | 564/449 |
| 3,153,088 | 10/1964 | Arthur | 564/462 |
| 3,155,724 | 11/1964 | Arthur | 564/462 |
| 3,384,661 | 5/1968 | Arthur | 564/303 |
| 3,393,236 | 7/1968 | Kuszewski | 564/303 |
| 3,789,032 | 1/1974 | Hoeschele | 560/352 X |

FOREIGN PATENT DOCUMENTS

| | | |
|---|---|---|
| 961049 | 1/1975 | Canada . |
| 971184 | 7/1975 | Canada . |
| 1220715 | 1/1971 | United Kingdom . |

OTHER PUBLICATIONS

Byrne et al., *Rubber Chemistry and Tech.*, vol. 58, (1985), pp. 985-996.
Wong et al., *Advances In Urethane Science and Tech.*, vol. 19, (1984), pp. 77-101.

Primary Examiner—Jose G. Dees
Assistant Examiner—Vera C. Clarke
Attorney, Agent, or Firm—Joseph C. Gil; N. Denise Brown

[57] ABSTRACT

The present invention is directed for preparing a 4,4'-diisocyanato dicyclohexylmethane which contain a relatively high amount of the trans,trans-isomer. The process broadly comprises (a) melting a mixture of 4,4'-diisocyanato dicyclohexyl-methane isomers, (b) cooling the melted mixture to form: (1) a liquid phase and (2) a solid phase, (c) removing said liquid phase, which is a commercially viable product itself, (d) heating the solid phase and removing that portion of the solid phase which has melted, and (e) recovering that portion of said solid phase which has not melted by heating the remaining portion.

9 Claims, No Drawings

MELT CRYSTALLIZATION PROCESS FOR PREPARING HIGH TRANS, TRANS-ISOMER CONTAINING 4,4'-DIISOCYANATO DICYCLOHEXYLMETHANE

CROSS REFERENCE TO RELATED APPLICATION

This application is a continuation of U.S. application Ser. No. 07/654,862 filed on Feb. 13, 1991, which is a continuation-in-part of U.S. application Ser. No. 07/513,698, filed on Apr. 24, 1990, both applications, now abandoned.

BACKGROUND OF THE INVENTION 4,4'-diisocyanato dicyclohexylmethane ("PICM") is a cycloaliphatic diisocyanate of low volatility. PICM and other aliphatic isocyanates are useful in the preparation of non-discoloring polyurethanes. In general, such isocyanates are reacted with glycols and/or polyols and chain extenders and/or cross linkers. Such isocyanates are particularly useful in the preparation of polyurethane coatings and elastomers. PICM and the diamine precursor, 4,4'-diaminodicyclohexylmethane ("PACM"), exist in three stereoisomeric forms (i.e., trans,trans; cis,trans; and cis,cis) as described, for example, in U.S. Pat. Nos. 2,606,925, and 3,789,032, Canadian Patents 961,049 and 971,184, and British Patent 1,220,715. Commercial grades of PACM normally contain all three isomers. The most direct method of producing PICM is to first hydrogenate diamino diphenylmethane to form a mixture of the stereoisomers of PACM, and to then phosgenate the mixture. When the synthesis of PICM is conducted using readily available mixtures of stereoisomers of PACM (such as the equilibrium mixture described in U.S. Pat. No. 3,155,724), the PICM obtained is a slurry at normal operating temperatures, having a melting point of about 58° C., which corresponds to a trans,trans-isomer content of about 54%. Various PICM mixtures are known in the art which have trans,trans-isomer contents of from about 18 to about 55% by weight. In addition, the art has recognized an advantage in utilizing high trans,trans-isomer PICM in producing elastomers (see, U.S. Pat. No. 3,789,032). In order to prepare PICM of relatively high trans,trans-isomer content, the art has generally used a PACM having a relatively high trans,trans-isomer content in the phosgenation reaction. Various methods are known for treating PACM to obtain the requisite high trans,trans-isomer content. Crystallization techniques have been described in the art. See, e.g., U.S. Pat. Nos. 2,494,563, 3,153,088, 3,384,661 and 3,393,236. The crystallization of PACM suffers from various disadvantages. PACM readily forms a precipitant when exposed to carbon dioxide, causing problems in filtering and contamination of the crystals (see, U.S. Pat. No. 2,494,563, column 3, lines 26-29, and column 4, lines 72-75). In addition, PACM is generally difficult to crystallize since it will easily form a supercooled liquid. The prior art has overcome this problem by adding seed crystals (U.S. Pat. No. 2,494,563), by lowering the viscosity by using an inert solvent (U.S. Pat. Nos. 2,494,563, 3,153,088, 3,393,236 and 3,384,661), or by forming an adduct of PACM that crystallizes better, such as the hydrate (U.S. Pat. No. 3,153,088) or the alcoholate (U.S. Pat. No. 3,384,661). Such an adduct must be treated to remove water or alcohol before phosgenating to PICM.

It is known to separate the trans,trans-isomer from an industrial mixtures of PICM having a trans,trans content of from 18 to 24% by weight by fractional crystallization followed by washing with cold hexane and then vacuum distillation. The mixture was cooled to 10° C. until crystallization took place and the solid fraction (the trans,trans-isomer) was removed by filtration in a nitrogen atmosphere. The residue was washed with cold hexane and stored under a nitrogen atmosphere. The filtrate was recooled and any new solids removed. See, Byrne et al, "A Study of Aliphatic Polyurethane Elastomers Prepared From Diisocyanate Isomer Mixtures," *Rubber Chemistry and Technology*, Vol. 58, 1985, pages 985-996, and Wong et al, "Structure-Property Relationships of Transparent Aliphatic Polyurethane Elastomers From the Geometric Isomers of Methylene bis(4-Cyclohexyl Isocyanate)," *Advances in Urethane Science and Technology*, Vol. 9, 1984, pages 77-101. The major disadvantage of this method is that solvent is required. In addition, the yield of the trans,trans-isomer is poor. Finally, cooling below room temperature is expensive on an industrial scale.

DESCRIPTION OF THE INVENTION

The present invention is directed to a relatively simple process for preparing a PICM containing a relatively high amount of the trans,trans-isomer, which process overcomes the problems associated with the prior art. More particularly, the present invention is directed to a process for the preparation of a 4,4'-diisocyanato dicyclohexylmethane containing at least by weight, and preferably at least 94% by weight, of the trans,trans-isomer comprising:

(a) melting a mixture of 4,4'-diisocyanato dicyclohexylmethane isomers containing at least 30% by weight, and preferably from 45 to 55% by weight, of the trans,trans-isomer, (b) cooling the melted mixture to a temperature of from about 0° to about 25° C. to form:
  (1) a liquid phase which contains from about 12 to about 25% by weight of the trans,trans-isomer, and
  (2) a solid phase which contains from about 70 to about 85% by weight of the trans,trans-isomer, (c) removing said liquid phase, which is a commercially viable product itself, (d) heating said solid phase to a temperature of from about 60 to the melting point of the pure trans,trans-isomer, which is about 83° C. (preferably over a period of from 3 to 5 hours and while maintaining that temperature for a period of from 1 to 2 hours), while removing that portion of said solid phase which has melted, with the melted material containing from about 35 to about 65% by weight, and preferably from about 45 to about 55% by weight, of the trans,-trans-isomer, and (e) recovering that portion of said solid phase which has not melted by heating the said remaining portion to a temperature of at least about 90° C. with the resultant product containing at least about 90% by weight, and preferably at least 94% by weight, of the trans,trans-isomer.

In one particularly preferred embodiment, the melted material of step (d) is recycled to step (a).

The presently preferred process comprises:

(a) melting a mixture of 4,4'-diisocyanato dicyclohexylmethane isomers containing at least 30% by weight, and preferably from 45 to 55% by weight, of the trans,trans-isomer,
(b) cooling the melted mixture to a temperature of from about 40° to about 45° C. for a time sufficient to allow crystallization to occur (generally for two to eight hours) and then subsequently cooling to a temperature of from about 0° to about 25° C. to form:
  (1) a liquid phase which contains from about 12 to about 25% by weight of the trans,trans-isomer, and
  (2) a solid phase which contains from about 70 to about 85% by weight of the trans,trans-isomer,
(c) removing said liquid phase, which is a commercially viable product,
(d1) heating said solid phase to a temperature of from about 65° to about 70° C. (and, preferably, maintaining that temperature for a period of from about 60 to about 120 minutes),
(d2) removing that portion of said solid phase which has melted, and
(e) recovering that portion of said solid phase which has not melted during step (d1) by heating the said remaining portion to a temperature of about 100° C. with the resultant product containing at least about 90% by weight, and preferably at least 94% by weight, of the trans,trans-isomer.

In a particularly preferred embodiment, the liquid phase of step (c) and the melted product removed during step (d2) are combined to make a liquid product.

Substantially any mixture of PICM containing at least 30% by weight, and preferably containing from 45 to 55% by weight, of the trans,trans-isomer can be used in step (a) of the process of the invention. It is generally preferred to utilize commercially available mixtures which typically contain about 50% by weight of the trans,trans-isomer. The particular mixture selected is melted, typically by heating to a temperature of from 60° to about 83° C., preferably for a period of from 120 to 180 minutes. The melted mixture is then cooled to a temperature of from about 0° to about 25° C. to form liquid and solid phases having the trans,trans-isomer contents noted above. Preferably, the melt is cooled to the requisite temperature in from 2 to 8 hours, and is held at that temperature for from 60 to 120 minutes.

The liquid and solid phases formed by cooling the melt can be separated by substantially any technique known in the art, such as, for example, filtration, decanting, centrifugation, or merely draining the liquid. The solid phase is then heated to a temperature equal to or less than the melting point of the pure product. This process is known to those familiar with the art as "sweating". The solid phase which has not melted is then recovered by heating to about 100° C.

The invention is not limited to a batch process and can also be performed in a continuous fashion through a series of heating and cooling cycles, e.g., as in a continuous crystallizer.

The invention is further illustrated but is not intended to be limited by the following examples in which all parts and percentages are by weight unless otherwise specified.

EXAMPLES

Example 1

3300 parts of a 4,4'-diisocyanato dicyclohexylmethane containing 50% by weight of the trans,trans-isomer were charged to a one gallon glass jar and completely melted at 80° C. The melt was then allowed to cool to room temperature (22° C.) and kept at that temperature for 16 hours. The liquid and solid phases were separated at room temperature by draining the liquid through a valve at the bottom of the vessel. The liquid phase contained 22.3% by weight of the trans,trans-isomer, while the solid phase contained 80.9% by weight of the trans,trans-isomer. The weight percent yields of liquid and solid phases were 53 and 47% respectively. The solid phase consisted of a three-dimensional matrix of crystals in the vessel.

The temperature of the vessel which contained the 1551 parts of the solid phase (i.e., 47% of 3300) was increased to 40° C. and held at that temperature for 2 hours. The fraction of the product that melted was drained. Then, the temperature was increased in 5° C. increments every two hours until a temperature of 80° C. was reached. The liquid generated was continuously drained during the heating step. When 80° C. was reached, the composition of the solid contained 93.8% by weight of the trans,trans-isomer. The weight percent yield with respect to the 1551 parts of the solid phase was 60%. The solid phase was removed from the glass jar by melting at a temperature of about 90° C.

Example 2

869 parts of a 4,4-diisocyanato dicyclohexylmethane containing 50% by weight of the trans,trans-isomer were charged to a jacketed column equipped with heating and cooling means. The material was completely melted at 80° C. and the melt was then allowed to cool to 45° C. and kept at that temperature for 8 hours. The solid and liquid phases were then cooled to 25° C. and held at that temperature for 4 hours. The liquid and solid phases were separated at this temperature by draining the liquid through a valve at the bottom of the column thereby obtaining 458 parts of liquid product. The solid phase was then heated to 45°–50° C. with 68.5 parts of melted product being removed. After two hours, the column was heated to 65° C. while removing an additional 25.5 parts of melted product. The liquid fractions were combined to form a liquid product that contained 24.2% by weight of the trans,trans-isomer. The remaining solid product (316 parts), which contained more than 90% by weight of the trans,trans-isomer was removed by heating the column to 100° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a 4,4'-diisocyanato dicyclohexylmethane containing at least 90% by weight of the trans,trans-isomer comprising:
  (a) melting a mixture of 4,4'-diisocyanato dicyclohexylmethane isomers containing at least 30% by weight of the trans,trans-isomer,
  (b) cooling the melted mixture to a temperature of from about 0° to about 25° C. to form:
    (1) a liquid phase which contains from about 12 to about 25% by weight of the trans,trans-isomer, and
    (2) a solid phase which contains from about 70 to about 85% by weight of the trans,trans-isomer,
  (c) removing said liquid phase,
  (d) heating said solid phase to a temperature of from about 60° to about 83° C. and removing that portion of said solid phase which has melted, with the melted material containing from about 35 to about 65% by weight, of the trans,trans-isomer, and (e) recovering that portion of said solid phase which has not melted by heating the said remaining portion to a temperature of at least about 90° C. with the resultant product containing at least about 90% by weight of the trans,trans-isomer.

2. The process of claim 1, wherein the mixture of step (a) contains from 45 to 55% by weight of the trans,-trans-isomer.

3. The process of claim 1, wherein the melted mixture removed in step (d) contains from 45 to 55% by weight of the trans,trans-isomer.

4. The process of claim 1, wherein the product recovered in step (e) contains at least 94% by weight of the trans,trans-isomer.

5. The process of claim 1, wherein the melted material of step (d) is returned to step (a).

6. A process for the preparation of a 4,4'-diisocyanato dicyclohexylmethane containing at least 90% by weight of the trans,trans-isomer comprising:

(a) melting a mixture of 4,4'-diisocyanato dicyclohexylmethane isomers containing at least 30% by weight of the trans,trans-isomer, (b) cooling the melted mixture to a temperature of from about 40° to about 45° C. for a period of time sufficient to allow crystallization to occur, and then subsequently cooling to a temperature of from about 0° to about 25° C. to form:

(1) a liquid phase which contains from about 12 to about 25% by weight of the trans,trans-isomer, and (2) a solid phase which contains from about 70 to about 85% by weight of the trans,trans-isomer, (c) removing said liquid phase, (d1) heating said solid phase to a temperature of from about 65° to about 70° C., (d2) removing that portion of said solid phase which has melted, and (e) recovering that portion of said solid phase which has not melted during step (d2) by heating the said remaining portion to a temperature of about 100° C. with the resultant product containing at least about 90% by weight of the trans,trans-isomer.

7. The process of claim 6, wherein the mixture of step (a) contains from 45 to 55% by weight of the trans,-trans-isomer.

8. The process of claim 6, wherein the product recovered in step (e) contains at least 94% by weight of the trans,trans-isomer.

9. The process of claim 6, wherein the liquid phase of step (c) and the melted product removed during step (d2) are combined to make a liquid product.

* * * * *